United States Patent
Moshe

[11] Patent Number: 6,111,415
[45] Date of Patent: Aug. 29, 2000

[54] DEVICE AND METHOD FOR DETERMINING THE MOISTURE CONTENT OF A BULK MATERIAL

[75] Inventor: Danny S. Moshe, Kiryat Ono, Israel

[73] Assignee: Malcam Ltd., Tel Aviv, Israel

[21] Appl. No.: 09/004,780

[22] Filed: Jan. 9, 1998

[51] Int. Cl.[7] .................................................. G01N 22/04
[52] U.S. Cl. .............................................. 324/640; 73/73
[58] Field of Search ..................... 324/637, 639, 324/640; 73/29.01, 29.05, 73

[56] References Cited

U.S. PATENT DOCUMENTS

| | | | |
|---|---|---|---|
| 2,659,860 | 11/1953 | Breazeale | 324/640 |
| 3,360,721 | 12/1967 | Pullman | 324/640 |
| 3,644,826 | 2/1972 | Cornetet, Jr. | 324/637 |
| 3,810,005 | 5/1974 | Bennion et al. | 324/639 |
| 3,815,019 | 6/1974 | Wiles | 324/640 |
| 3,829,764 | 8/1974 | Bosisio | 324/632 |
| 4,123,702 | 10/1978 | Kinanen et al. | |
| 4,352,059 | 9/1982 | Suh et al. | 324/664 |
| 4,361,801 | 11/1982 | Meyer et al. | 324/640 |
| 4,500,835 | 2/1985 | Heikkila | 324/637 |
| 4,546,311 | 10/1985 | Knochel | 324/640 |
| 4,578,998 | 4/1986 | Gard | 73/73 |
| 4,620,146 | 10/1986 | Ishikawa et al. | 324/640 |
| 4,675,595 | 6/1987 | Hane | 324/640 |
| 4,789,820 | 12/1988 | Parrent, Jr. et al. | 324/640 |
| 4,962,384 | 10/1990 | Walker | 324/640 |
| 4,991,915 | 2/1991 | Thompson et al. | 324/640 |
| 5,333,493 | 8/1994 | Cutmore | 324/640 |
| 5,581,191 | 12/1996 | Yamaguchi | 324/640 |
| 5,619,143 | 4/1997 | Stevens et al. | 324/639 |
| 5,621,330 | 4/1997 | Greenwald et al. | 324/640 |
| 5,845,529 | 12/1998 | Moshe et al. | 73/73 |

Primary Examiner—Diep N. Do
Attorney, Agent, or Firm—Mark M. Friedman

[57] ABSTRACT

A method and system for measuring the moisture content and internal structure of a material which is either packaged as a module or presented in a continues bulk flow. A frequency modulated digital pulse of very high frequency microwaves is directed through the material under analysis by a microwave transmitter. A microwave receiver receives the microwave signal after it exits the material on the opposite side to that of the microwave transmitter. The attenuation and time delay of the exit signal are analyzed and corrected with empirically derived functions so as to calculate the moisture content and density, respectively, of the material. Irregularity of the internal structure of the material is determined by comparing the calculated densities of multiple slices of the material with each other. In an alternative embodiment, the microwave signal is transmitted through the material under analysis by a first satellite dish antenna, and then redirected back through the same slice of material by a second satellite dish antenna located on the opposite side of the material under analysis. The returning signal is received by the first satellite dish antenna, and then processed to calculate the density and moisture of the material in the same manner as described above.

22 Claims, 8 Drawing Sheets

DEVICE AND METHOD FOR DETERMINING THE MOISTURE CONTENT OF A BULK MATERIAL

FIELD AND BACKGROUND OF THE INVENTION

The present invention relates to the field of non-invasive characterization of the nature of materials and, more particularly, to an apparatus and method for determining the moisture content of a bulk of non-homogeneous material.

Many different types of synthetic and organic materials are the basis for the formation of many different manufactured products. These materials must be gathered, transported and stored before being used in the manufacturing process. The manufacturing process itself may require multiple procedures, first to prepare the raw material, and then to use the processed material in the formation of the actual product. Many of these procedures are dependent upon the moisture content of the material. If the moisture content is too high, for example, the material may decompose during storage and transportation, before it can be used. If the moisture content is too low, processing and use of the material may be difficult.

Synthetic and organic non-homogenous materials whose behavior depends upon their moisture content include cotton, paper, wool, seeds, pharmaceuticals and synthetic fibers. For example, cotton is processed to separate the desired cotton from contaminating materials such as seeds, and is then spun into fibers for use in textile manufacture. For such processing and spinning to be successful, the cotton fibers should have an even moisture content that is neither too high nor too low. For example, fibers with low moisture content are weaker, breaking more frequently.

Cotton is typically transported and stored in the form of large bales or cases, hereinafter collectively referred to as modules. In addition, certain manufacturing processes entail processing of synthetic or natural materials, such as cotton, in a continues flow of bulk material, as on a conveyer belt system. The optimum moisture content of the cotton fibers for the production of textiles is from 6.5 to 8% before spinning and between 6–20% once packaged as a module, depending upon the requirements of the subsequent processing steps. Thus, effective moisture control in the textile mill depends upon accurate measurement of the moisture content of the fibers of the modules or the continuos bulk flow.

Non-invasive moisture measurements may be performed using microwave radiation. Typically, a microwave radiation source is located on one side of the cotton module, and a receiving antenna is located on the opposite side of the module. The radiation source beam is transmitted through a portion of the module and is received by the receiving antenna, which then produces a signal. This signal is used to determine the moisture content of that portion of the module and the mass uniformity of the module.

When the material being analyzed is of very high density and relatively uniform internal structure, such as the sheets of paper constituting the paper web output of a paper making machine, the moisture on the surface of the material acts as a mirror, particularly when the moisture content is relatively high (greater than 20%). In such a circumstance, incident microwave radiation may be reflected of off the surfaces of the material in a predictable manner, and the difference between reflected radiation and transmitted radiation (transmitted radiation being the radiation passing through the substance under analysis) can be used to measure moisture content. A device for measuring moisture content in this manner has been disclosed in U.S. Pat. No. 4,789,820 to Parrent Jr et al. Such a device, however, is unsuitable for use with poorly reflective materials, that is, materials of relatively non-uniform internal structure, lower moisture content, and lower density, such as modules of cotton, wool, seeds, pharmaceuticals and synthetic fibers.

Typically, microwave measurement of the moisture content of modules of non-uniform material is achieved by analyzing the characteristics of the attenuated transmitted microwave signal only, after it has passed through the module under analysis. A method for performing such moisture measurements is disclosed in U.S. Pat. No. 5,621,330 to Greenwald et al, which patent is incorporated herein. In Greenwald et al, the phase shift of the microwaves received by the receiving antenna is analyzed so as to determine the density of the material under analysis. The moisture content of the material is then calculated from the density data in conjunction with data describing the attenuation of the microwaves received by the receiving antenna, that is, the transmitted microwaves.

Calculating moisture based on measuring the phase shift of transmitted microwaves, however, suffers from several deficiencies:

1. The phase shift measuring apparatus is only capable of describing phase shifts within the phase region between 0 and $2\pi$. Depending on the nature of the material being analyzed, however, the true phase shift is often in a region greater than $2\pi$. As such, it is necessary to determine the phase region before calculating the phase shift for a transmitted microwave, so as to perform an appropriate correction. The determination of phase region is performed by analyzing the progressive change in phase shift which occurs as the leading edge of the module under analysis first enters the beam of microwave radiation being emitted by the moisture measuring device, inducing an "edge effect" on the received microwave signal. In the case of a continuos flow of bulk material, however (as opposed to individual modules), the absence of frequent leading edge effects precludes frequent calibrations to compensate for changes in phase region, thus rendering phase shift calculations inaccurate. As such, phase shift measuring devices are only suitable for use when individual modules are being analyzed, but cannot be used for analyzing a continues flow of bulk materials.

2. As each component of the phase shift measuring apparatus induces a phase shift of its own when processing the recorded signal, it is necessary to compensate for this effect when first constructing the device. As it is not feasible to recheck and adjust the phase region compensation once the device is in use, it is desirable that the components of the device not undergo spontaneous "drift" to a significant degree over time. As such, it is necessary to use components of the highest quality when constructing the device. Phase shift measuring devices are thus expensive and, due to the possibility of drift occurring, potentially unreliable in the long term.

3. The need to perform phase region compensation and phase shift calculation requires that specialized components be incorporated into the device. As a result, the device is complex to manufacture, thus adding to its expense.

4. Due to resolution difficulties, measurement of phase shift is unreliable in low density materials.

There is thus a widely recognized need for a device for non-invasively measuring the moisture content of a non-homogenous material, which is cheaper, less complex, and more reliable than current devices which measure microwave phase shift, which is capable of analyzing materials of low density as well as higher density, and which is capable of analyzing a continues flow of bulk materials in addition to individual modules of bulk materials.

SUMMARY OF THE INVENTION

The current invention is a system and method for measuring the moisture content of a material using microwave radiation, in which density data is derived from an analysis of the time delay induced in a transmitted microwave signal, rather than from an analysis of the phase shift.

It is therefore an object of the current invention to provide a method and apparatus for inexpensively and reliably measuring the moisture content of a non-homogenous material. It is a further object of the current invention to provide a moisture measuring device and method which is capable of analyzing materials of low density as well as higher density. It is a yet further object of the current invention to provide a moisture measuring device and method which is capable of analyzing a continuos flow of bulk material as well as analyzing individual modules of bulk material. It is a still further object of the current invention to provide an accurate moisture measuring apparatus and method.

According to the teachings of the present invention, therefore, there is provided a method for determining a moisture content of a material, the method including the steps of transmitting a plurality of microwaves through a portion of the material; receiving the transmitted microwaves after the transmitted microwaves have exited the portion of the material; determining an acquired attenuation and an acquired time delay of the received microwaves relative to the transmitted microwaves; calculating a raw moisture content of the material from the acquired attenuation value; calculating a density of the material from the acquired time delay value; and calculating a true moisture content of the material from the raw moisture content and from the density of the material.

There is further provided a system for determining a moisture content of a material, including a microwave transmission and reception mechanism, located on one side of the material, operative to transmit a plurality of microwaves through a portion of the material in a first direction, and to receive a plurality of microwaves exiting the same portion of the material in a second direction, the second direction being a substantially opposite direction to the first direction; a microwave antenna, located on an opposing side of the material to the first microwave antenna, and operative to direct a plurality of microwaves through the same portion of the material in the second direction, the directed plurality of microwaves being the transmitted plurality of microwaves after exiting the portion of the material; and a microwave processing mechanism, operative to process the received plurality of microwaves to determine a true moisture content of the material.

There is also provided a method for determining a moisture content of a material, including the steps of:

(a) transmitting a plurality of microwaves from a first side of the material, in a first direction, through a portion of the material;

(b) directing said transmitted plurality of microwaves from an opposite side of the material, in a second direction, through said same portion of the material, said second direction being a substantially opposite direction to said first direction;

(c) receiving, on said first side of the material, said directed microwaves; and (d) processing said received microwaves to calculate a true moisture content of the material.

Hereinafter, the term "material" includes any material which can be stored in a module or processed in a continuos bulk flow. For example, cotton, wool, silk and synthetic fibers, as well as paper, can all be stored in modules. Pharmaceutical materials, such as powdered medications, can also be stored in a "module", although such a module would probably be a box of powder. Hereinafter, the term "bale" refers to any structure in which material is present in pressed layers and tied with ties wrapped around the structure. Hereinafter the term "bobbin" refers to any structure which contains a hollow core around which material is present. Hereinafter, the term "module" refers to any discrete unit of material, including bales, boxes, bobbins and the like, and can be contrasted with a "bulk flow" of material, by which is meant that the material is not packaged in discrete units, but is rather transported in a continues bulk, such as occurs when a material is continuosly fed onto a moving conveyer belt.

The principles and operation of a method and a apparatus according to the present invention may be better understood with reference to the drawings and the accompanying description.

DESCRIPTION OF THE PREFERRED EMBODIMENTS

The present invention is of a method and an apparatus which can be used to measure the moisture content and the internal structure of a bulk material packaged in a module or in a continuos flow, as along a conveyer belt.

Figure 1:
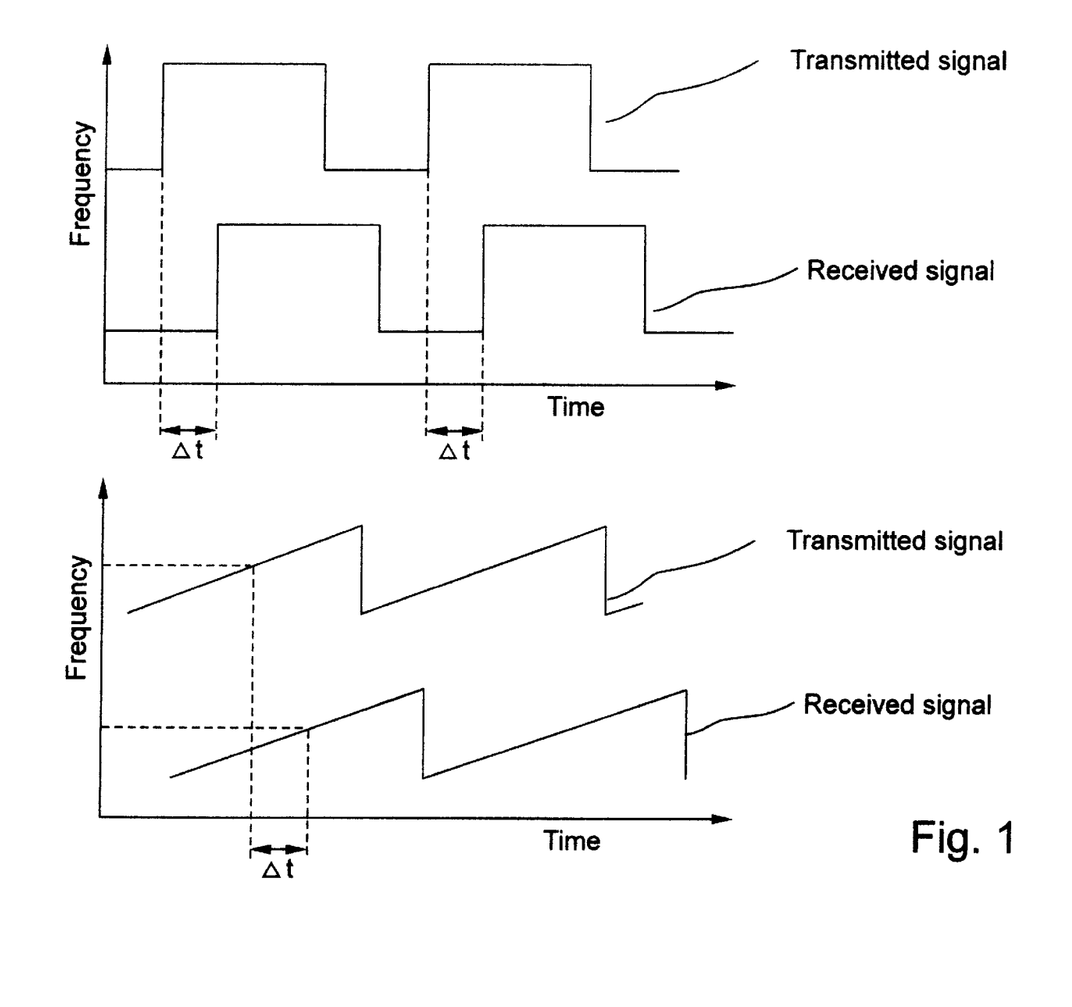
FIGS. 1A and 1B are illustrations of the principle of time delay measurement of a received microwave signal.

The method according to the current invention entails measurement of the time delay of a received very high frequency microwave signal. The upper graph of FIG. 1A plots the change in frequency over time of a source microwave signal that has been transmitted through a bulk of material. As can be seen, the signal is transmitted in defined digital pulses, by which is meant that the signal commences and ends at defined points in time. The lower graph in FIG. 1A plots the same microwave signal as received by a receiving antenna after having been transmitted through a bulk of material. The velocity of signal transmission depends on the density of the material as well as the nature of the material in question. When synchronously comparing the onset of the transmitted and received signals, therefore, a time delay (Δt) can be discerned, which is a function of the density of the material. An alternative method for measuring Δt is depicted in FIG. 1B. In this example, the signal pulse comprises continuously changing frequencies, rather than a single frequency. As such, measurement of t can be achieved by comparing the timing of any particular frequency in both signals, as shown. Hereinafter, a transmitted signal pulse comprising continuously changing frequencies, as illustrated in FIG. 1B, rather than a single frequency, is referred to as a "frequency modulated pulse".

As will be well known to one familiar with the field, and as disclosed in U.S. Pat. No. 5,621,330 to Greenwald et al, the degree of attenuation of a received microwave signal is affected, in part, by the moisture content of the material through which the signal has been transmitted. Other factors influencing received signal attenuation are the nature of the material, its weight, its temperature and its density. It is therefore possible to calculate the moisture content of a material by analyzing several known parameters (i.e. the weight and temperature of the material, and empiric data describing the type of material) along with two measured parameters, namely, the Δt of a received microwave signal (from which can be calculated the density of the material at the point of measurement), and the attenuation of a received microwave signal.

Figure 2:
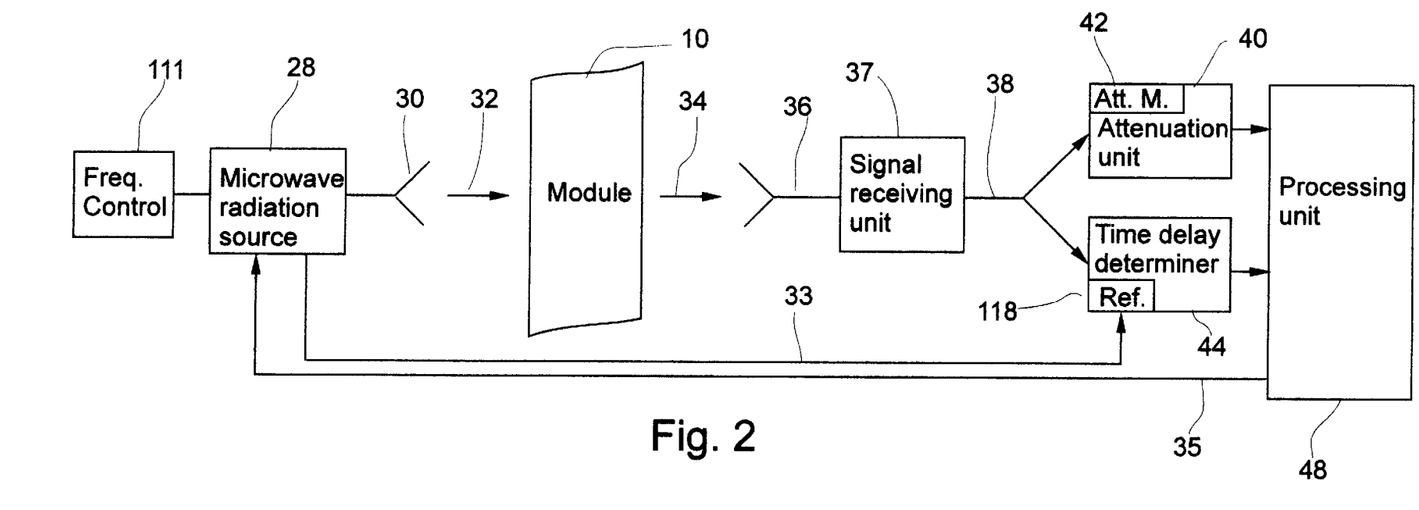
FIG. 2 is a block diagram illustrating one embodiment of a apparatus which can be used with the method of the present invention.

FIG. 2 shows an exemplary apparatus for performing the moisture measurements of the present invention. The apparatus includes a microwave radiation source 28, shown on one side of a module 10 of material under analysis. In a preferred embodiment, microwave radiation source 28 is a multiple-frequency transmitter for sequentially transmitting microwave radiation at a plurality of frequencies. The frequency to be transmitted is selected by a frequency controller 111. It will be appreciated that module 10 can be replaced with a continuous flow of bulk material without departing from the principles of the invention, however, for purposes of illustration, the apparatus will be described only with reference to module 10. Microwave radiation source 28 preferably includes at least one source antenna 30 for transmitting a source signal 32. In the preferred embodiment, source signal 32 is a very high frequency microwave signal in the form of a frequency modulated digital pulse. The preferred frequency for source signal 32 depends on the nature of the material being examined. For large modules, a frequency of 1.5–2 GHz is suitable. For average sized bales or cases of material, a frequency in the range of 3.5 GHz is suitable. For small cases of material, a frequency of 10–16 GHz is suitable. For bulk materials with low density, such as pharmaceutical powders, 16–30 GHz is suitable. For a single location in module 10 multiple pulses are transmitted by source antenna 30. Hereinafter, a group of multiple signal pulses transmitted through one location of module 10 will be said to constitute a "slice" or a "portion" of module 10, and multiple slices or portions will be said to make up an "area" of module 10.

Source signal 32 is directed through module 10, and passes out of module 10 as an exit signal 34. As source signal 32 passes through module 10, source signal 32 is both attenuated and slowed. As mentioned above, the extent of this attenuation is determined by the density of the material of module 10 encountered by source signal 32, and by the moisture content of the material of module 10 encountered by source signal 32. The degree to which source signal 32 is slowed is determined by the density of module 10. Exit signal 34 is received by at least one receiving antenna 36 connected to a signal receiving unit 37. In a preferred embodiment, source antenna 30 and receiving antenna 36 are lens antennae. Suitable examples of lens antennae are a "horn antenna" (Malcam Ltd. Tel Aviv, Israel) and a "flat printed antenna" (MTI Ltd. Tel Aviv, Israel). An advantage to using a lens antenna is that the emitted microwave signal is more focused than the signal emitted by a regular antenna. A narrower, focused microwave beam enables the examination of lower density materials than can be examined using a regular antenna. Receiving antenna 36 is located on a substantially opposite side of module 10 relative to source antenna 30. In a preferred embodiment, signal receiving unit 37 includes a heterodyne receiver.

After signal receiving unit 37 has received exit signal 34, it produces an antenna signal 38. Antenna signal 38 then goes to an attenuation unit 40. Attenuation unit 40 includes an attenuation measurer 42, which compares the amplitude of antenna signal 38 to the known amplitude of source signal 32, thus measuring the attenuation of source signal 32 caused by its passing through the material of module 10.

At least a part of antenna signal 38 also goes to a time delay determiner 44. Time delay determiner 44 includes a reference receiver 118 which receives a reference signal 33 directly from microwave radiation source 28, via a cable. Reference signal 33 is thus identical to source signal 32 in terms of its timing and frequencies. Time delay determiner 44 compares reference signal 33 with antenna signal 38 so as to determine the time delay of antenna signal 38, that is, the degree to which source signal 32 was slowed while passing through module 10. In the preferred embodiment, the determination of the time delay of antenna signal 38 by time delay determiner 44 is achieved by utilizing a low pass filter and zero crossing. These techniques will be well known to one familiar with the art. The signal attenuation, as calculated by attenuation measurer 42, and the time delay, as calculated by time delay determiner 44, are then input to a processing unit 48. The attenuation and the time delay of antenna signal 38 are used by processing unit 48 to determine the moisture content and local density of module 10. The algorithms used to perform these calculations are described in FIG. 4, below. A graphic or numeric output describing these parameters is then displayed on a display (not shown). Processing unit 48 sends a feedback signal 35, describing antenna signal 38, to microwave radiation source 28. After processing feedback signal 35, microwave radiation source 28 changes the nature of source signal 32 so as to optimize antenna signal 38. Such optimization may include changing the frequency and/or the direction of the electric field density of source signal 32, and may be implemented, for example, so as to control background noise or minimize external radio frequency interference (such as that generated by a nearby cellular phone).

As described above, the signal attenuation is used to determine a raw moisture content (i.e. a moisture value which is uncorrected for the effect of density), while the signal time delay is used to determine the internal structure (i.e. the density) of the material under analysis. More specifically, it can be said that although the time delay of a signal alone cannot be translated into an absolute density value for a material, changes in the time delay of a signal do reflect changes in the density of that material. Thus if a standard density of a material and its associated time delay are known, any change in that density, relative to its standard density, can be calculated from a measured change in the signal time delay for that material.

Figure 3:
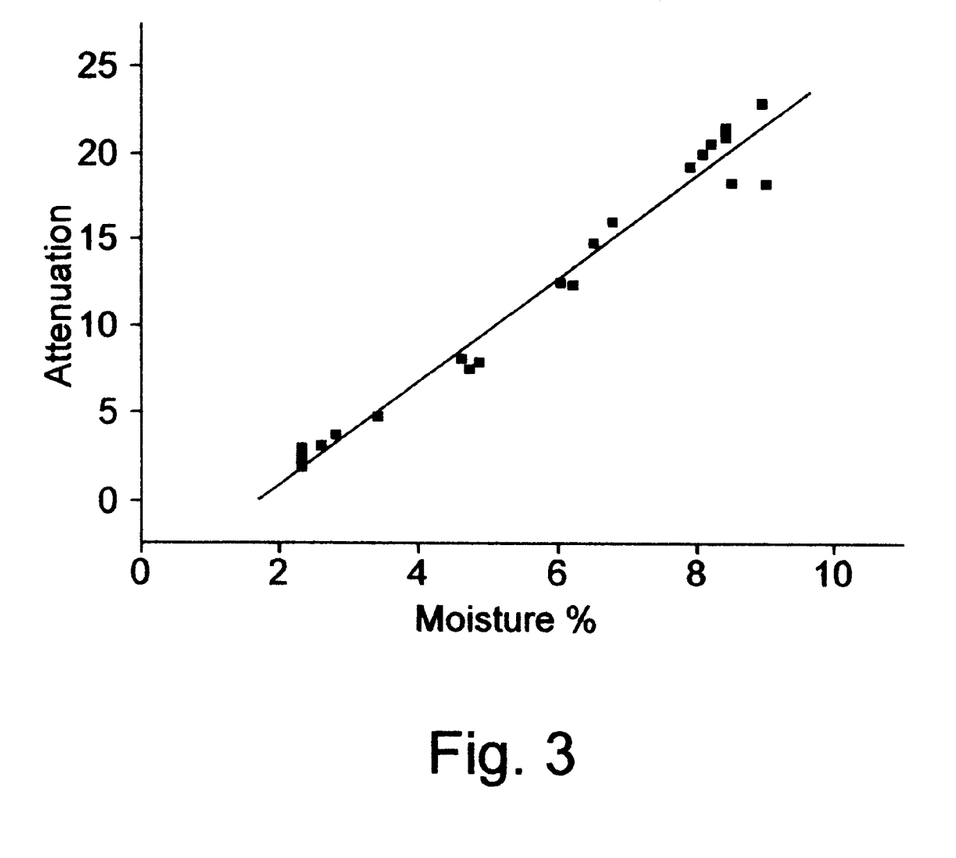
FIG. 3 is a graph showing the agreement between the true moisture content and the corrected signal attenuation, as calculated according to the method of FIG. 4.

The signal attenuation is translated into a value for raw moisture content in accordance with empirical information derived from a database. An example of such a correlation is shown in FIG. 3. Empirically derived correlations of this nature must be generated for essentially all materials suitable for analysis by the current invention. For each type of material, such correlations are empirically determined on a test material at a specific temperature and of a specific density. For a given type of material under analysis by the current invention, however, the actual temperature of the material at the time of analysis may differ from that of the test material used to derive the empiric correlation for that type of material. So too, the actual density of a material under analysis may differ from the density of the test material used to derive the appropriate empiric correlation. When analyzing a material with the current invention, therefore, it is necessary to first correct the measured attenuation and time delay values for any density and temperature variations (so as to replicate the conditions under which the empiric correlation was derived from the test material), prior to applying the relevant empiric correlations translating time delay into density, and attenuation into moisture content.

Both the attenuation and the time delay are thus used in combination with empirically determined correction factors to calculate the final moisture content of the material under analysis.

Figure 4:
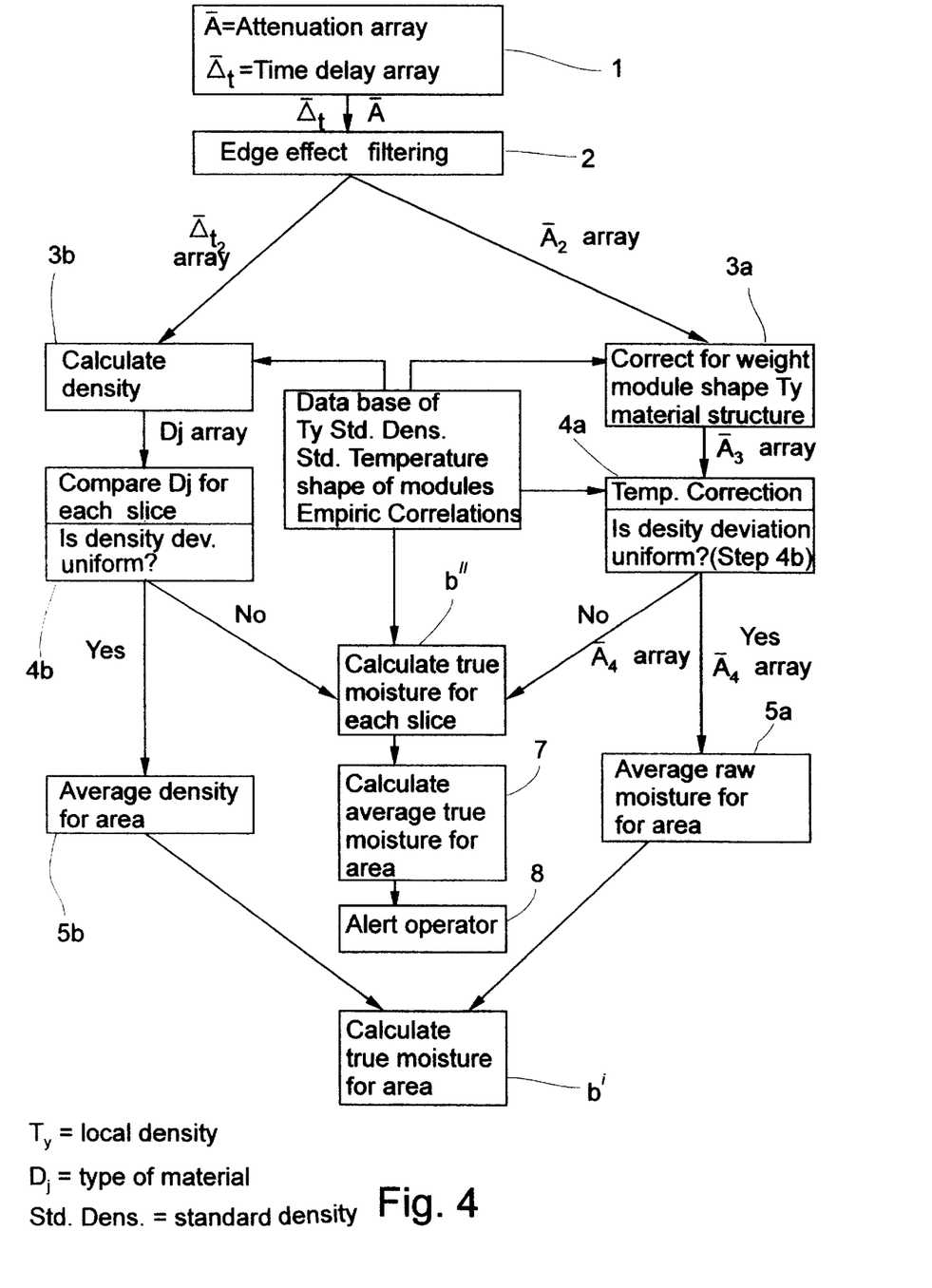
FIG. 4 is a flow chart of the method of calculating the moisture content of the material.

FIG. 4 shows a flow chart of the calculations for determining the moisture content and the internal structure (that is, the local density and variations in density) of the material in module 10.

The first step in the flow chart is the generation of an array of attenuation values (A) and an array of time delay values ($\Delta t$), as shown in step 1, by scanning an area of the material, that is, by generating multiple slices each consisting of a plurality of microwave pulses, as described above in FIG. 2. Several slices are grouped together as an "area", the moisture content and density of which it is desired to calculate. In step 2 the data points in each array are filtered to remove any "edge" effects, the importance of which is illustrated below in FIG. 5. This results in filtered arrays $A_2$ and $\Delta t_2$. The determination of whether a particular set of data points represents an edge effect can be made in a number of ways. For example, the location of module 10 relative to source signal 32 can be determined, such that when an edge of module 10 is about to pass through source signal 32, a signal is sent to processing unit 48. Alternatively and preferably, the measurement of the attenuation can be plotted, and the data points corresponding to any artefactually high peaks or low troughs of attenuation can be eliminated, for example by removing any values which are more than two or three standard deviations from the average attenuation.

The flow chart then branches into two parts. The right branch shows the steps used in calculating the raw moisture content of the material, while the left branch shows the steps used for the determination of the internal structure of the material. For clarity, steps in the right (moisture content) branch will have the letter "a" appended; e.g., "3a", "4a", etc. Steps in the left (internal structure) branch will have the letter "b" appended; e.g., "3b", "4b", etc.

Following the right branch, in step 3a the attenuation array for each slice is corrected for the effect of the shape of the module, the type of material being analyzed, and optionally for the density of the material. This correction is based upon empirically determined factors stored in a database, and produces an array $A_3$ of density, shape and type corrected attenuation values. When the material under analysis is in the form of a module of known size, optional density correction is achieved by comparing the measured gross weight of the module to a standard gross weight for a module of that size and type of material. Density correction is thus calculated by dividing the measured weight of the material into the standard weight value. When the material under analysis is in the format of a continuous flow of bulk material, however, rather than individual modules, measurement of the gross weight of the area under analysis is not feasible. In this circumstance, or when it is decided not to correct for density of a module, the density of the material is assumed to be the same as the standard density stored in the database, and density correction is not performed.

Next, in step 4a, array $A_3$ is corrected for the current measured temperature of the material, to produce a temperature-corrected attenuation array $A_4$ for each slice. The function for this correction is proportional to $1-Ts/Tt$, where Ts is the standard temperature (stored in a database), and Tt is the measured temperature. The temperature-corrected attenuation array $A_4$ is thus compensated for the effect of measurements acquired at temperatures which differ from the temperature at which the empiric correlation, for that material type, was derived.

At this point in the flow diagram, the result of step 4b (which will be explained below) determines whether the algorithm continues to step 5a or step 6". In the event that, as determined in step 4b, the deviation in the calculated densities for a plurality of slices is relatively small, the algorithm continues to step 5a. In this step, the complete set of all attenuation values (i.e. array $A_4$) for all slices constituting a single area of material is used to calculate a raw moisture value or content for that area. This calculation is performed according to a function which can be a linear integration of all the attenuation values for all the acquired slices, or else a polynomial, depending upon such empirical factors as the type of material being measured, the shape of the module and the structure of the module. This raw moisture value will be used in the determination of the true moisture value or content (by which is meant the raw moisture value corrected for the effect of material density) for the area of material under analysis. However, the true moisture value cannot be determined without knowing the actual density of material, which is calculated as shown in the left branch of the flow chart. In the event that, as determined in step 4b, the deviation in the calculated densities for a plurality of slices is significant, the algorithm continues to step 6", which will be explained below.

Turning now to the left branch of FIG. 4, the steps for calculating the density of the material under analysis are shown. In step 3b the density of each slice is calculated from the measured, filtered time delay array $\Delta t_2$ for each slice, in accordance with empirical information derived from a database. The empirical information includes the type of material, shape of the module (if relevant), a standard density for the material, and an empirical correlation between time delay and density. The empirical correlation between time delay and density is obtained by collecting time delay data from an analysis of a test material having known density, and then comparing the calculated density values with the true, known density values for the test material. From this analysis of the test material, the proper correlation between measured time delay values and calculated density values can be determined. Since this correlation depends upon the density and geometry of the test shape, and upon the nature of the material or materials from which the test shape is constructed, such an analysis must be performed for substantially every desired shape and material in order to obtain these essentially empirical correlations.

In step 4b, the difference between the density of the current slice and that of previous slices is determined. Such deviations are important because they reveal irregularities in the internal structure of the material and/or the presence of foreign bodies located within the material. Based on the uniformity, or lack thereof, of density values for the slices constituting an area under analysis, the area is categorized as being of either uniform or non-uniform (by which is meant irregular) density.

The density of the area of material is calculated by one of two different methods, depending upon whether the density of the area is categorized as being uniform or as being non-uniform. In the event that the deviation in the calculated densities for a plurality of slices is relatively small, the density is categorized as being uniform. A single mean density value is then calculated, and used to represent the density of the area. In step 6', the average density value and the average raw moisture value, which was calculated in step 5a, are combined to determine the true moisture value. The true moisture value is a function of the average density, the average raw moisture value, and an empirically determined correlation factor stored in a database. This correlation factor depends upon the type and structure of material, and is empirically determined through experimentation, as described above for the empiric correlation between time delay and density.

In the event that the deviation in the calculated densities for a plurality of slices is relatively large, the density is categorized as being non-uniform or irregular. In this instance, as shown in step 6", the density value for each individual slice or portion is combined with the raw moisture value for each individual slice or portion (as calculated in step 4a) to determine an array of true moisture values for the individual slices constituting the area under analysis. This calculation is performed in a manner analogous to that described above for uniform density calculations, except that a plurality of density values, and preferably all density values, are used for the calculations. A density value for an individual slice or portion is hereinafter referred to as a "portion density value", and a raw moisture value for an individual slice or portion is hereinafter referred to as a "portion density value". In step 7, an average true moisture value for the area under analysis is then calculated as the mean of the array of true moisture values for the individual slices constituting the area under analysis.

The true moisture value or values, and/or average true moisture value, calculated in steps 6', 6", and 7, are then output, for example by displaying on a display unit which could include a video screen, or by other apparatus for displaying the information. In the event that the density of the slices is not uniform, a warning to this effect is displayed on the display output (step 8). The reason for this warning is to alert the operator to the fact that the displayed moisture value has not been calculated from data derived from multiple slices (which is thus more accurate and less influenced by random error) but rather, it has been calculated from data derived from a single slice only (and is thus less accurate and more sensitive to error).

It will be understood that a second system 26 may be deployed in an orientation which is orthogonal to that of a first system 26, so as to calculate moisture and density data for slices through module 10, such that such slices are orthogonal to and coordinated with the slices scanned by the first system 26. The resultant density and moisture data from the plurality of intersecting slices can be correlated with each other by processing unit 48 so as to generate 2 or 3 dimensional maps of density and moisture within the material being analyzed. A potential source of inaccuracy in the calculation of signal attenuation may arise due to microwave signals which have undergone multiple reflections within and around module 10, including reflections off of source antenna 30, being received by signal receiving unit 37. Such microwaves will hereinafter be referred to as "scattered" microwaves. The attenuation of scattered microwaves does not provide an accurate depiction of the moisture content within module 10. Scattered microwaves originating from a given pulse of microwave radiation may be identified by the fact that they are received by receiving unit 37 later than non-scattered microwaves originating from the same microwave pulse. A reference time delay value, which predicts when non-scattered microwaves will be received by signal receiving unit 37, can be empirically determined for essentially any material type and shape, and stored in a database. Microwave signals received at a point in time NOT predicted by the reference time delay value can therefore be assumed to be scattered microwaves. In an alternative embodiment of the current invention, therefore, attenuation measurer 40 accesses a database of reference time delay values and a scatter determiner module (not shown) in attenuation measurer 40, and compares the actual time delay of the received signal to a reference time delay value, so as to determine whether the received microwave signals are scattered or not. Only non-scattered microwaves are then processed by attenuation measurer 40. In this way, the number of distorted microwave signals analyzed by attenuation measurer 40 when determining the attenuation of received microwaves can be minimized.

The equations describing the relationship between time delay and material density are as follows. Note that F is the frequency of the microwave radiation; l is the length of the beam path as it passes through the material of the module; $\epsilon'$ (or e') is the dielectric constant of the bulk of material; $\epsilon''$ (or $\epsilon''$) is the attenuation constant of a bulk material under analysis; $\epsilon_o$ (or $\epsilon_o$) is the vacuum dielectric constant; $\Delta t$ is the time delay of a microwave signal after passing through a material under analysis; C is the speed of microwaves through a material under analysis; $C_o$ is the speed of reference signal 35 as relayed through the cable connecting microwave radiation source 28 with reference receiver 118 ($\approx$speed of light); d is the density of a material under analysis; m is the moisture of a material under analysis; $\lambda$ is the wavelength of the microwave radiation; and $f$ represents the phrase "is a finction of . . .".

1. $\lambda = C/F$
2. Both $\epsilon'$ and $\epsilon''$ are functions of d and m, however $\epsilon'$ is only minimally influenced by m. Therefore:
   $\epsilon' \approx f(d, m) \approx f(d)$
   $\epsilon'' \approx f(d, m)$
3. The relationship between $\epsilon'$ and $\epsilon''$ is thus largely a function of moisture content of the material (m):

$$\frac{\epsilon''}{\epsilon'} \approx f(m)$$

4. As $C_O > C$:

$$\Delta t \approx \frac{l}{C} - \frac{l}{C_o}$$

5. $C \approx \dfrac{C_o}{\varepsilon'} \ (\varepsilon' > 1)$

6. $\Delta t \approx \dfrac{l}{C_o}(\varepsilon' - \varepsilon_o) \approx \dfrac{l}{C_0}(\varepsilon' - 1)$ 7. $\varepsilon' \approx \left(\dfrac{C_o}{l}\right) \cdot \Delta t + 1 \approx f(d)$ FIG. 5 is an illustration of edge effects and foreign body effects on attenuation data derived from multiple microwave slices through module 10. Similar effects are encountered for time delay data as well.

Figure 5A:
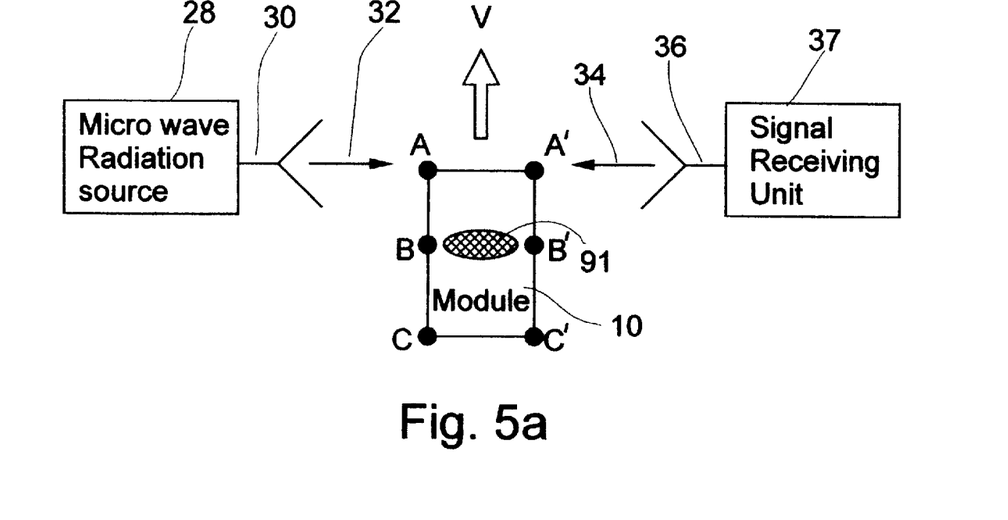
FIGS. 5A and 5B illustrate the influence of edges and foreign bodies on measured time delay and attenuation data.

FIG. 5A shows module 10 moving in direction V between microwave radiation source 28, which emits source signal 32, and receiving antenna 36, which receives exit signal 34. A foreign body 91 is within module 10. The length of module 10 is from point A to point C.

Figure 5B:
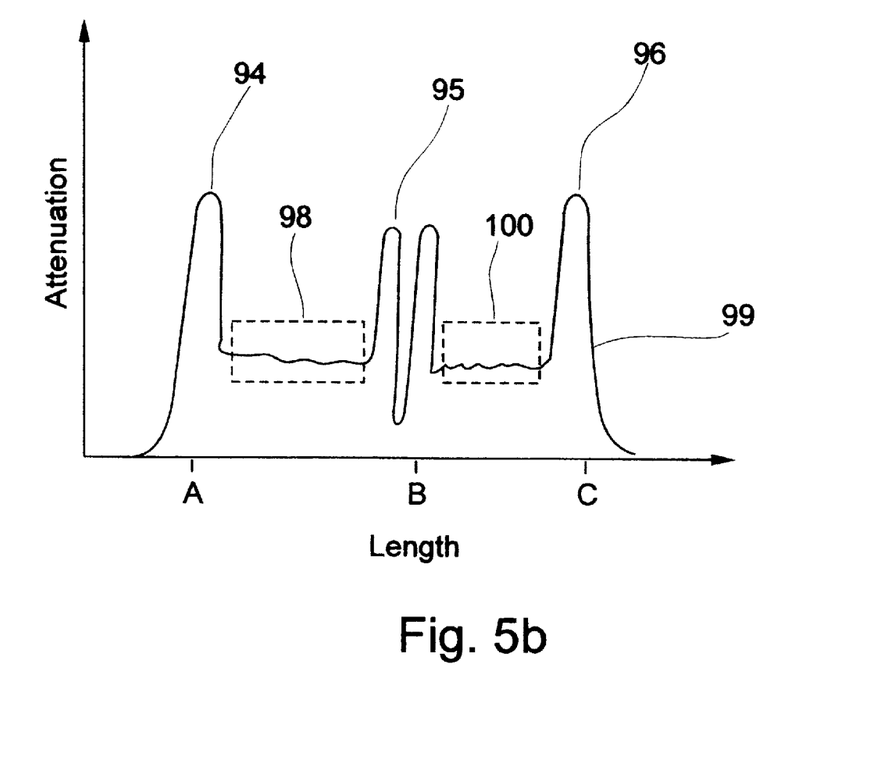

FIG. 5B shows a graph 99 of the measured attenuation obtained substantially for all slices along the length of module 10. A first peak 94 occurs as module 10 first enters source signal 32, corresponding to a slice between points A and A', and is artefactually high due to a leading edge effect. So too a peak 96 is caused by the trailing edge of module 10, at slice C–C', as module 10 leaves source signal 32. A slice B–B' passing through foreign body 91 causes an artefact 95. As peaks 94 and 96 are artefactual, they cannot be used for determining the corrected attenuation, and hence the raw moisture value, as described in FIG. 4 above, and are thus filtered out as described in step 2 of FIG. 4. Thus, the data points which are used for determining the attenuation are taken from between peaks 94, 95, and 96, as shown by box 98 and box 100.

Figure 6A:
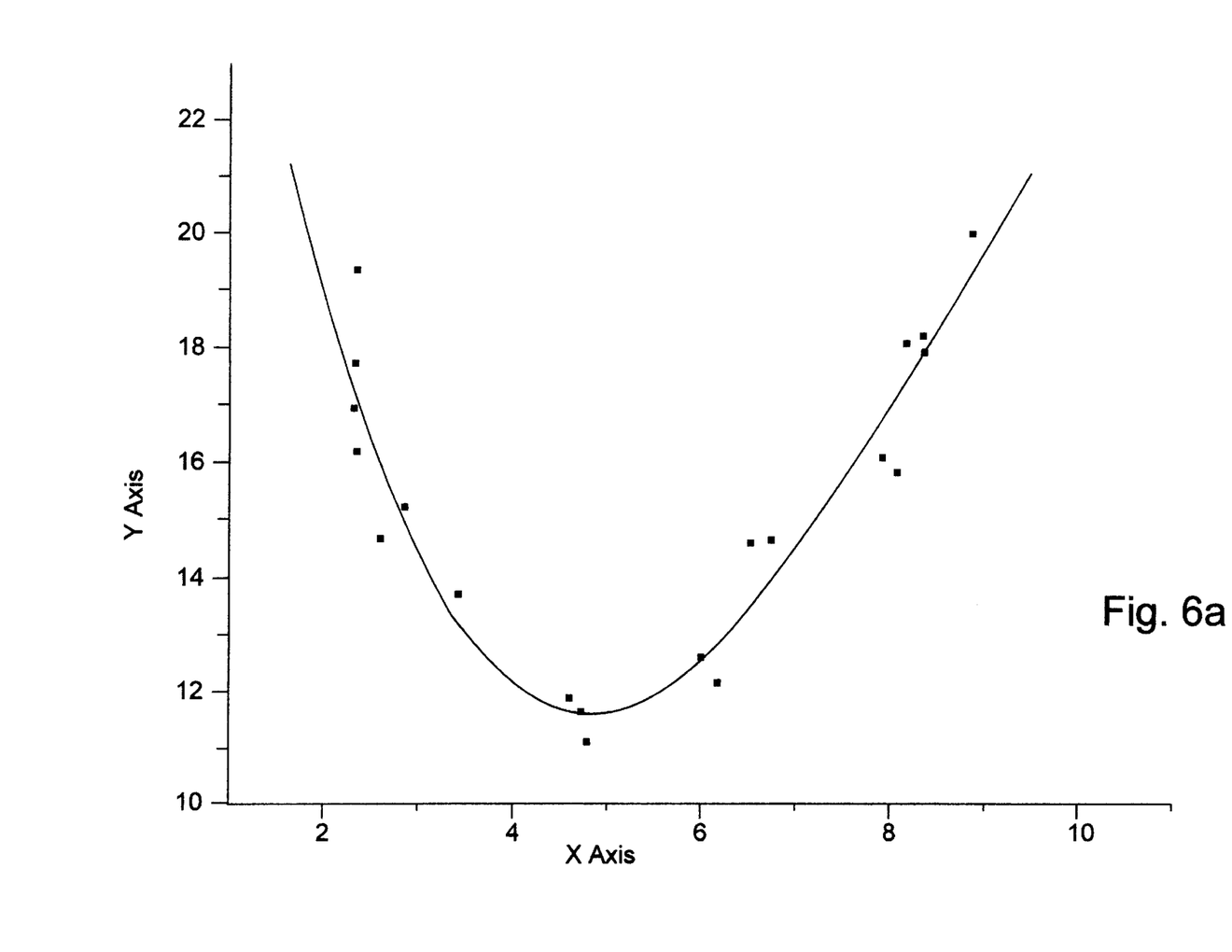
FIGS. 6A and 6B are graphs showing the relationship between measured attenuation and true moisture content for slices including and excluding an edge of a module.
Figure 6B:
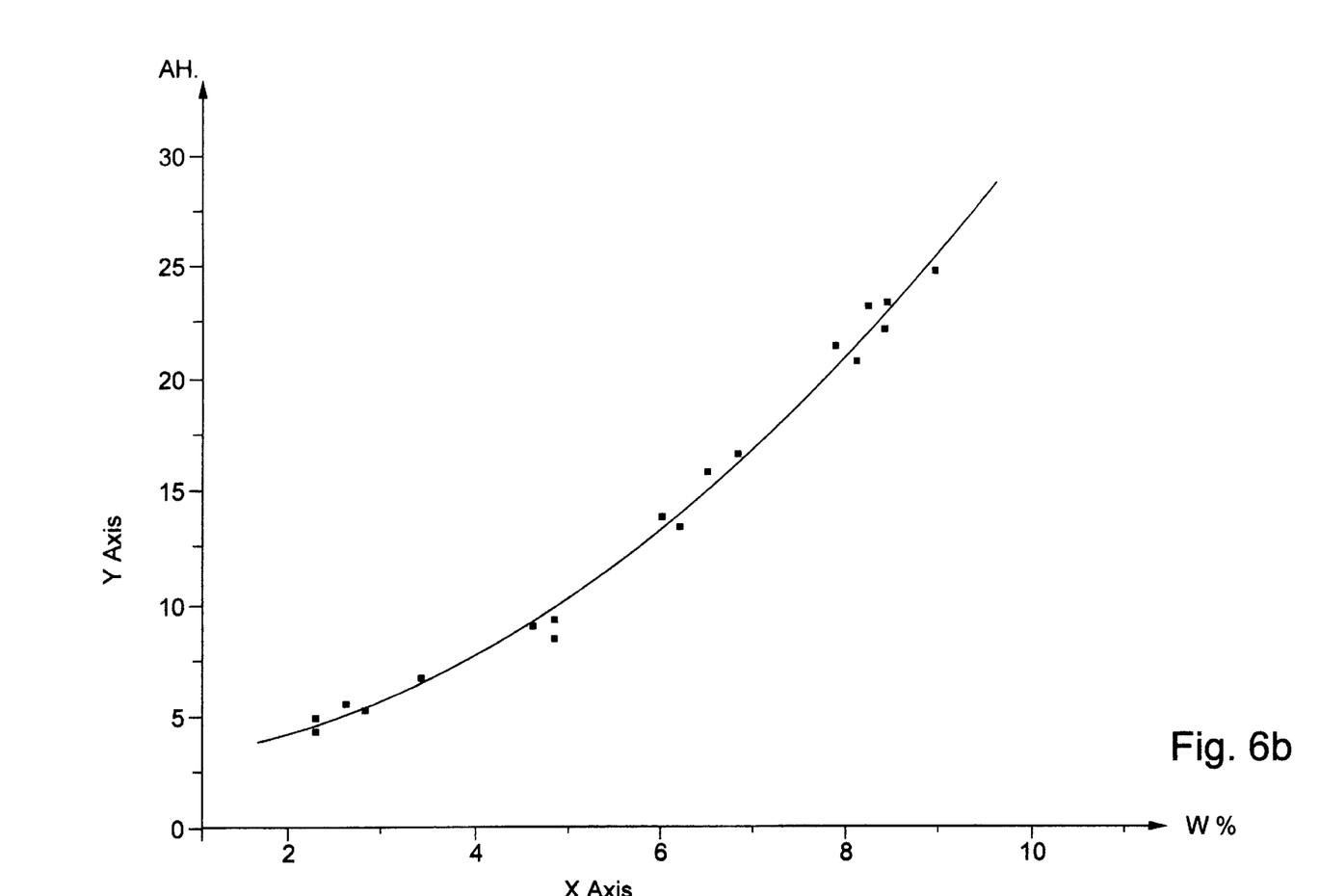

FIGS. 6A and 6B demonstrate the importance of selecting a particular portion of the measured attenuation for calculating the moisture of the material. In FIG. 6A, the curve shows the relationship between true moisture values (plotted along the X-axis) and the measured attenuation obtained from one of the artefactually high peaks described in FIG. 5 (plotted on the Y-axis). Clearly, there is no correlation between the actual moisture content of the material and the artefactual measurements obtained from the peaks. By contrast, FIG. 6B shows the relationship between true moisture values (on the X-axis) and the measured attenuation (on the Y-axis) obtained from an area between the peaks, as for example box 100. The correlation is clearly very high, since the true moisture and the measured attenuation rise in a nearly linear fashion. Thus, the measured attenuation is an accurate reflection of the true moisture content of a material only when artefactual measurements, such as those caused by leading or trailing edge effects or foreign bodies, are filtered out.

Figure 7:
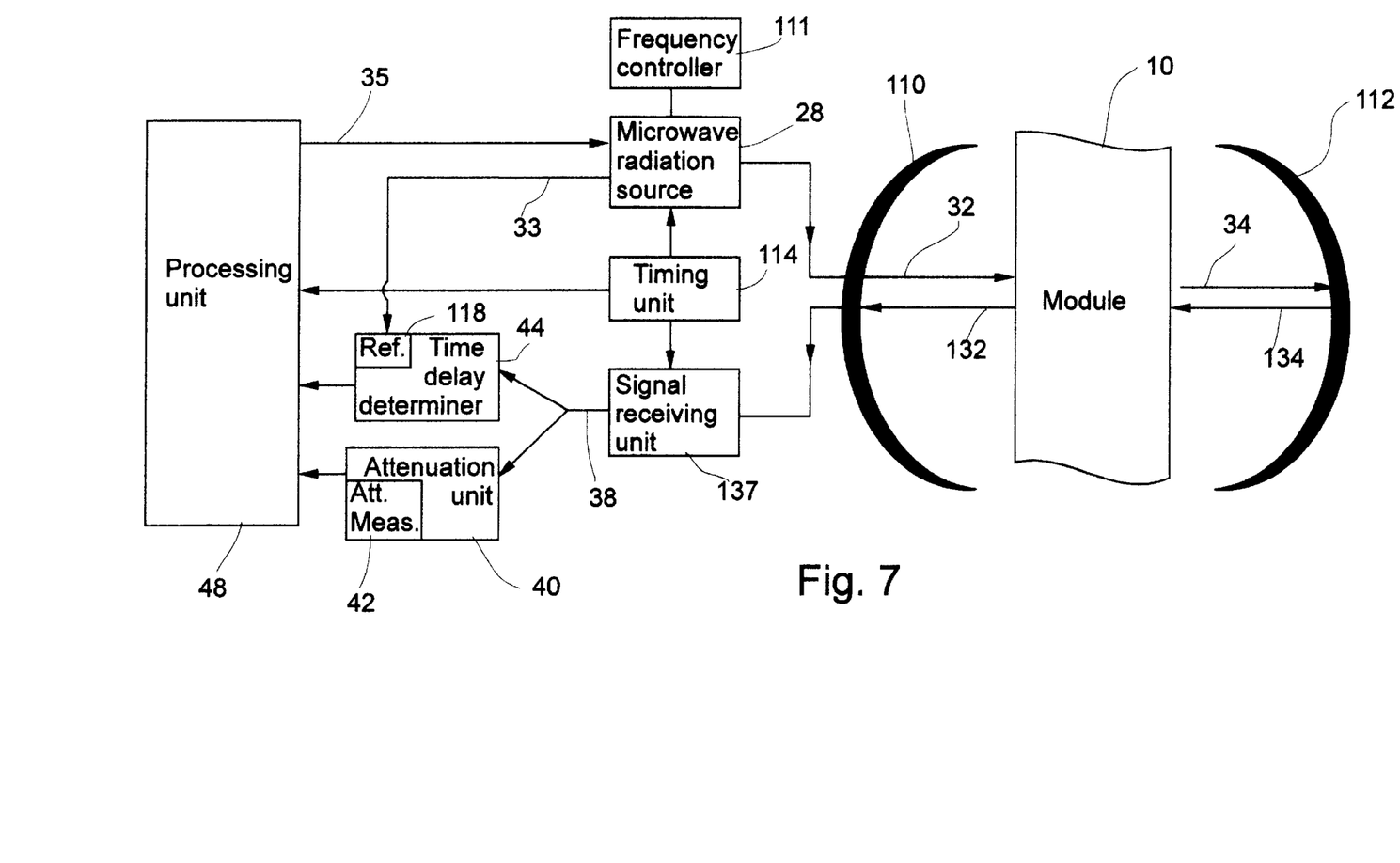
FIG. 7 is a block diagram illustrating a second embodiment of a apparatus which can be used with the method of the present invention, in which a satellite dish antenna is used to reflect the transmitted signal back through the material under analysis.

FIG. 7 demonstrates a second embodiment of the current invention in which a microwave signal is transmitted through a material under analysis and then reflected back through the same slice of material before being processed. The amount of material traversed by the microwave signal is therefore doubled. Consequently, the degree of signal attenuation and the acquired time delay are more pronounced, which enhances the accuracy of attenuation and time delay measurements.

This second embodiment includes a microwave radiation source 28. In a preferred embodiment, microwave radiation source 28 is a multiple-frequency transmitter for sequentially transmitting microwave radiation at a plurality of frequencies. The frequency to be transmitted is selected by a frequency controller 111. Microwave radiation source 28 is connected to a first antenna 110, and causes first antenna 110 to transmit a source signal 32. In the preferred embodiment, source signal 32 is a very high frequency microwave signal in the form of a frequency modulated digital pulse.

Source signal 32 is directed through a module 10 of material under analysis, and passes out of module 10 as an exit signal 34. It will be appreciated that module 10 can be replaced with a continuous flow of bulk material without departing from the principles of the invention, however, for purposes of illustration, the apparatus will be described only with reference to module 10. Exit signal 34 is received by a second antenna 112, located on a substantially opposing side of module 10 relative to first antenna 110. In the preferred embodiment, first and second antennae 110 and 112 are satellite dish antennae, although any antenna or mechanism capable of reflecting a received signal back through the material it had just traversed could be used as second antennae 112, and any antenna capable of transmitting and receiving a microwave signal could be used as first antenna 110. Standard satellite dishes of radius 40 cm and curvature 2 m, such as the "Reflector Dish Antenna" (Malcam Ltd. Tel Aviv, Israel), are suitable for use as first and second satellite dish antennae 110 and 112.

When second antenna 112 receives exit signal 34, it immediately redirects exit signal 34, as reflected signal 134, back into module 10. Exit signal 34 may be redirected by second antenna 112 either by a process of reflection, or by a process of receiving exit signal 34 and then transmitting reflected signal 134 at a frequency, amplitude and timing identical to that of received exit signal 34. Reflected signal 134 passes out of module 10 as exit reflected signal 132, and is received by first antenna 110. In the preferred embodiment, therefore, first antenna 110 constitutes a microwave transmission and reception mechanism. By "microwave transmission and reception mechanism" is meant any mechanism capable of both transmitting a microwave signal, and receiving a microwave signal.

In an alternative embodiment, first antenna 110 is replaced with two antennae, one for transmitting source signal 32, and the other for receiving exit reflected signal 132. In this circumstance, the transmitting antenna need not be a satellite dish antenna, but could be a lens antenna of the type described previously. In this embodiment, therefore, the two antennae together constitute a microwave transmission and reception mechanism.

In the preferred embodiment, first antenna 110 relays exit reflected signal to a signal receiving unit 137, which produces an antenna signal 38. Antenna signal 38 then goes to an attenuation unit 40. Attenuation unit 40 includes an attenuation measurer 42, which compares the amplitude of antenna signal 38 to the known amplitude of source signal 32, thus measuring the attenuation of source signal 32 caused by its passing through the material of module 10 in both directions.

At least a part of antenna signal 38 also goes to a time delay determiner is 44. Time delay determiner 44 includes a reference receiver 118 which receives a reference signal 33 directly from microwave radiation source 28. Reference signal 33 is thus identical to source signal 32 in terms of its timing and frequencies. Time delay determiner 44 compares reference signal 33 with antenna signal 38 so as to determine the time delay of antenna signal 38, that is, the degree to which source signal 32 was slowed while passing through module 10. The signal attenuation, as calculated by attenuation measurer 42, and the time delay, as calculated by time delay determiner 44, are then input to a processing unit 48. The attenuation and the time delay of antenna signal 38 are used by processing unit 48 to determine the moisture content and local density of module 10, as described in FIG. 4, above. A graphic or numeric output describing these parameters is then displayed on a display (not shown). Processing unit 48 sends a feedback signal 35, describing antenna signal 38, to reference receiver 118 and microwave radiation source 28. After processing feedback signal 35, microwave radiation source 28 changes the nature of source signal 32 so as to optimize antenna signal 38 and maximize the sensitivity of the moisture content measurements. Such optimization may include changing the frequency and/or the direction of the electric field density of source signal 32, and may be implemented, for example, so as to control background noise, minimize external radio frequency interference (such as that generated by a nearby cellular phone), and/or minimize the effects on antenna signal 38 of a foreign body within module 10. A timing unit 114 may optionally be incorporated into the current invention. Timing unit 114 coordinates the signal transmission and reception functions of signal receiving unit 136 and microwave radiation source 28. It will be appreciated that although the method and system of apparatus 126 have been described with regard to the measurement of time delay of a transmitted microwave signal, the same method may be used for enhancing the measurement of phase shift of a transmitted microwave signal, as is done in the prior art.

Therefore, there has been described a system and method for measuring the moisture content of a non-homogenous material, based on the measurement of the time delay of a transmitted microwave signal. As the mechanism for measuring time delay is relatively simple and does not alter the signal itself, complex calibration and compensation processes are not necessary, as is the case when measuring phase shift. The apparatus is thus cheaper to manufacture, and more reliable in the long term (as "drift" of calibration over time is not relevant). Furthermore, as "leading edge" effects are not necessary for calibration purposes, the method is suitable for use both on modules and on a continues flow of bulk material, in which there are no leading edges. As there are no phase shift related resolution difficulties, the method is suitable for use with materials of both low and higher density. An additional feature of the current invention is the use of a satellite dish antenna to reflect the transmitted microwave signal back through the material being analyzed before recording and processing the signal (as opposed to current apparatuss in which the signal traverses the material in one direction only), thus enhancing acquired changes in signal attenuation and time delay for each analysis "slice" and improving measurement accuracy.

While the invention has been described with respect to a limited number of embodiments, it will be appreciated that many variations, modifications and other applications of the invention may be made.

What is claimed is:

1. A method of determining a moisture content of a material, the method comprising the steps of:
   (a) transmitting a plurality of microwaves through a portion of the material;
   (b) receiving said transmitted microwaves after said transmitted microwaves have exited said portion of the material;
   (c) determining an acquired attenuation value and an acquired time delay value of said received microwaves relative to said transmitted microwaves;
   (d) calculating a raw moisture content of the material from said acquired attenuation value;
   (e) calculating a density of the material from said acquired time delay value; and
   (f) calculating a true moisture content of the material from said raw moisture content and from said density of the material.

2. The method of claim 1, further comprising the steps of:
   (g) repeating steps (a) to (c) for a plurality of portions of the material, such that a plurality of acquired attenuation values and a plurality of acquired time delay values are obtained;
   (h) calculating a raw moisture content of the material from said plurality of acquired attenuation values;
   (i) calculating a density of the material from said plurality of acquired time delay values; and
   (j) calculating a true moisture content of the material from said raw moisture content and from said density of the material.

3. The method of claim 1, further comprising the steps of:
   (g) correcting said acquired attenuation value for density of the material, temperature of the material, type of the material, and structure of the material, by utilizing at least one empirical factor, said correcting producing a corrected attenuation value;
   (h) correcting said acquired time delay value for type of material and a standard density of the material, by utilizing at least one empirical factor, said correcting producing a corrected time delay value;
   (i) calculating a corrected raw moisture content of the material from said corrected attenuation value;
   (j) calculating a corrected density of the material from said corrected time delay value; and
   (k) calculating a corrected true moisture content of the material from said corrected raw moisture content and from said corrected density of the material.

4. The method of claim 2, wherein said portion of the material is part of a module of the material.

5. The method of claim 4, further comprising the step of filtering said plurality of time delay values and said plurality of attenuation values so as to remove artifactual values caused by said plurality of microwaves passing through an edge of said module.

6. The method of claim 1, wherein said portion of the material is part of a continuos bulk flow of the material.

7. The method of claim 2, further comprising the steps of
   (k) calculating a raw moisture content value from an attenuation value for each of said plurality of portions of the material, such that a plurality of portion raw moisture content values is obtained;
   (l) calculating a density value from a time delay value for each of said plurality of portions of the material, such that a plurality of portion density values is obtained;
   (m) comparing each of said portion density values with each other of said portion density values to determine a regularity of a structure of the material, said structure being determined to be irregular if any of said portion density values are substantially different from any other of said portion density values.

8. The method of claim 7, wherein, when said structure is determined to be irregular, a true moisture content is calculated for each of said plurality of portions of the material, from said plurality of portion density values and from said plurality of portion raw moisture content values.

9. The method of claim 1, wherein said transmitted microwaves are transmitted as a digital pulse of very high frequency microwaves.

10. The method of claim 9, wherein the frequency of said digital pulse is constantly changing.

11. The method of claim 1, wherein said raw moisture content of the material is calculated from said attenuation value utilizing an empirically derived correlation between signal attenuation and material moisture content.

12. The method of claim 1, wherein the material is selected from the group consisting of cotton fiber, silk fiber, wool fiber, pharmaceutical material, seeds, paper, tobacco and synthetic fiber.

13. The method of claim 1, further comprising the step of (g) providing a reference time delay value; and (h) identifying scattered microwaves within said received microwaves by comparing said acquired time delay to said reference time delay value.

14. A system for determining a moisture content of a material, comprising:

(i) at least one microwave transmission and reception mechanism, located on one side of the material, operative to transmit a plurality of microwaves through a portion of the material in a first direction, and to receive a plurality of microwaves exiting the same portion of the material in a second direction, said second direction being a substantially opposite direction to said first direction;

(ii) at least one microwave antenna located on an opposing side of the material to said at least one microwave transmission and reception mechanism, and operative to direct a plurality of microwaves through said same portion of the material in said second direction, said directed plurality of microwaves being said transmitted plurality of microwaves after exiting said portion of the material; and (iii) a microwave processing mechanism, operative to determine a true moisture content of the material by measuring a time delay and an attenuation of said received plurality of microwaves, calculating a density of the material from said time delay, and calculating a raw moisture content of the material from said attenuation.

15. The system of claim 14, wherein at least one of said microwave antenna and said microwave transmission and reception mechanism includes a satellite dish antenna.

16. The system of claim 14, wherein said transmitted plurality of microwaves is a frequency modulated digital pulse of very high frequency microwaves.

17. The system of claim 14, wherein said at least one microwave antenna is further operative to reflect said transmitted plurality of microwaves, after said transmitted plurality of microwaves has exited said portion of the material, through said same portion of the material in said second direction.

18. The system of claim 14, further comprising (d) a timing mechanism, operative to synchronize the transmitting and receiving of microwave signals by said microwave transmission and reception mechanism.

19. A method of determining a moisture content of a material, comprising the steps of:

(i) transmitting a plurality of microwaves from a first side of the material, in a first direction, through a portion of the material;

(ii) directing said transmitted plurality of microwaves from an opposite side of the material, in a second direction, through said same portion of the material, said second direction being a substantially opposite direction to said first direction;

(iii) receiving, on said first side of the material, said directed microwave; and (iv) processing said received microwaves to calculate a true moisture content of the material, wherein said processing of said received microwaves includes measuring a time delay and an attenuation of said received microwaves, calculating a density of the material from said time delay, and calculating a raw moisture content of the material from said attenuation.

20. The method of claim 19, wherein said plurality of microwaves are transmitted as a frequency modulated digital pulse of very high frequency microwaves.

21. The method of claim 19, wherein said transmitting and said receiving are executed by a single microwave antenna.

22. The method of claim 19, wherein said directing is achieved by reflecting said transmitted plurality of microwaves.

* * * * *